(12) United States Patent
Nam et al.

(10) Patent No.: US 9,562,891 B2
(45) Date of Patent: Feb. 7, 2017

(54) METHOD FOR SCREENING PATIENT-SPECIFIC ANTI-CANCER AGENT USING LIMITING DILUTION ASSAY

(71) Applicant: Samsung Life Public Welfare Foundation, Seoul (KR)

(72) Inventors: Do Hyun Nam, Seoul (KR); Kyeung Min Joo, Seoul (KR); YeonSook Choi, Seoul (KR)

(73) Assignee: SAMSUNG LIFE PUBLIC WELFARE FOUNDATION, Seoul (KR)

(*) Notice: Subject to any disclaimer, the term of this patent is extended or adjusted under 35 U.S.C. 154(b) by 0 days.

(21) Appl. No.: 14/228,205

(22) Filed: Mar. 27, 2014

(65) Prior Publication Data
US 2015/0101070 A1    Apr. 9, 2015

(30) Foreign Application Priority Data
Oct. 8, 2013    (KR) ........................ 10-2013-0120118

(51) Int. Cl.
*G01N 33/74* (2006.01)
*A61P 35/00* (2006.01)
*G01N 33/50* (2006.01)

(52) U.S. Cl.
CPC ................................ *G01N 33/5011* (2013.01)

(58) Field of Classification Search
None
See application file for complete search history.

(56) References Cited

U.S. PATENT DOCUMENTS 6,194,158 B1 * 2/2001 Kroes ................... C12Q 1/6809
435/6.16
2012/0077698 A1    3/2012 Abbud-Antaki

OTHER PUBLICATIONS

Xu et al, Three-dimensional in vitro tumor models for cancer research and drug evaluation, Biotechnology Advances 32 (2014) 1256-1268.*
Lovitt et al, Advanced Cell Culture Techniques for Cancer Drug Discovery, Biology 2014, 3, 345-367.*
Choi et al, Lessons from patient-derived xenografts for better in vitro modeling of human cancer, Advanced Drug Delivery Reviews, 2014, pp. 222-237.*
Hidalgo et al, Patient-Derived Xenograft Models: An Emerging Platform for Translational Cancer Research, Cancer Discovery, 4(9), 2014, pp. 1-16.*
Burdett et al, Engineering Tumors: A Tissue Engineering Perspective in Cancer Biology, Tissue Engineering: Part B vol. 16, No. 3, 2010.*
Caicedo-Carvajal CE, Liu Q, Goy A, Pecora A, Suh KS, Three-Dimensional Cell Culture Models for Biomarker Discoveries and Cancer Research. Translational Medicine, 2012, pp. 1-8.*
Nakamura et al, Evaluation of drug toxicity with hepatocytes cultured in a micro-space cell culture system, Journal of Bioscience and Bioengineering vol. 111 No. 1, 78-84, 2011.*
Friedrich, J., Seidel, C., Ebner, R., and Kunz-Schughart, L.A. Spheroid-based drug screen: considerations and practical approach. Nat Protoc 4, 309-324, 2009.*
Sainz et al, Standing Out from the Crowd: Cancer Stem Cells in Hepatocellular Carcinoma, Cancer Cell 23, Apr. 15, 2013, pp. 431-433.*
Li et al, Microfluidic 3D cell culture: potential application for tissue based bioassays, Bioanalysis. Jun. 2012 ; 4(12): 1509-1525.*
Alterovitz, G., et al., "Personalized medicine for mucositis: Bayesian networks identify unique gene clusters which predict the response to gamma-D-glutamyl-L-tryptophan (SCV-07) for the attenuation of chemoradiation-induced oral mucositis", "Oral Oncology", Aug. 6, 2011, pp. 951-955, vol. 47.
Arnedos, M., et al., "The challenge to bring personalized cancer medicine from clinical trials into routine clinical practice: The case of the Institut Gustave Roussy", "Molecular Oncology", Mar. 16, 2012, pp. 204-210, vol. 6.
Black, A., et al., "Personalized medicine in metastatic non-small-cell lung cancer: promising targets and current clinical trials", "Current Oncology", Jun. 2012, pp. S73-S85, vol. 19, Supplement 1.
Bonnet, D., et al., "Human acute myeloid leukemia is organized as a hierarchy that originates from a primitive hematopoietic cell", "Nature Medicine", Jul. 1997, pp. 730-737, vol. 3, No. 7.
De Wever, O., et al. , "Role of tissue stroma in cancer cell invasion", "Journal of Pathology", 2003, pp. 429-447, vol. 200.
Hausser, H., et al., "Phenotypic instability of Saos-2 cells in long-term culture", "Biochemical and Biophysical Research Communications", May 31, 2005, pp. 216-222, vol. 333.
Kondo, T. et al., "Persistence of a small subpopulation of cancer stem-like cells in the C6 glioma cell line", PNAS , Jan. 20, 2004, pp. 781-786, vol. 101, No. 3.
Lee, D., et al., "LDA(Limited Dilution Assay) Micropillar/well Chip using 3D patient-drived cell culture", "MEMS", Apr. 4, 2013, pp. 1-2 (English Abstract).
Rao, J., "Molecular Mechanisms of Glioma Invasiveness: The Role of Proteases", "Nature Reviews: Cancer", Jul. 2003, pp. 489-501, vol. 3.
Rubio-Viqueira, B., et al., "Direct In Vivo Xenograft Tumor Model for Predicting Chemotherapeutic Drug Response in Cancer Patients", "Clinical Pharmacology and Therapeutics", Feb. 2009, pp. 217-221, vol. 85, No. 2.
Sanai, N., et al., "Neural Stem Cells and the Origin of Gliomas", "N Engl J Med", Aug. 25, 2005, pp. 811-822, vol. 353.
Singh, S., et al., "Identification of human brain tumour initiating cells", "Nature", Nov. 18, 2004, pp. 396-401, vol. 432.

* cited by examiner

*Primary Examiner* — Maria Marvich
(74) *Attorney, Agent, or Firm* — Hultquist, PLLC; Mary B. Grant

(57) ABSTRACT

A screening method is described for selecting patient-specific anti-cancer agents reflecting individual genetic properties, in a precise and rapid manner, using an extremely small amount of cancer cells. Such screening method is useful for development of novel anti-cancer agents and the personalized medical field.

14 Claims, 5 Drawing Sheets

METHOD FOR SCREENING PATIENT-SPECIFIC ANTI-CANCER AGENT USING LIMITING DILUTION ASSAY

CROSS-REFERENCE TO RELATED APPLICATION

This application claims priority under the provisions of 35 USC 119 to Korean Patent Application No. 10-2013-0120118 filed Oct. 8, 2013. The disclosure of Korean Patent Application No. 10-2013-0120118 is hereby incorporated herein by reference, in its entirety, for all purposes.

TECHNICAL FIELD

The present invention relates to a screening method for precisely and efficiently selecting patient-specific anti-cancer agents, and more specifically, to a screening method of patient-specific anti-cancer agents using a limiting dilution assay (LDA) characterized by three-dimensional culturing an small amount of patient-derived cancer cells together with anti-cancer agents, automatically analyzing the sphere formed therefrom, and selecting the patient-specific anti-cancer agent.

BACKGROUND ART

Cancer is a term commonly known as a disease occurring due to indiscreet proliferation of cells and due to damage to the mechanism of regulating cell proliferation. In accordance with data released by World Health Organization (WHO) in February, 2012, the number of deaths due to cancer throughout the world in 2008 was about 7.6 million people accounting for 13% of mortality over the world and, and five cancers such as lung cancer, stomach cancer, liver cancer, colon cancer and breast cancer account for about 50% of the entire death rate of cancer. In addition, it was shown that 12.7 million new cancer patients were diagnosed during 2008, and among them, about 70% occurred in underdeveloped/developing countries such as China, South America, Africa, and the like. The occurrence rate of new cancer patients has steadily increased, such that it is expected to reach 22 million cancer patients in 2030.

In particular, the occurrence rate of cancer patients in Asia has rapidly increased from obesity due to westernized diet, an increase in intake of red meat and alcohol, and the like. It is expected that the occurrence rate of cancer patients per 100,000 people will rapidly increase from 122 people in 2005 to 163 people in 2030 by 45% or more, which is about 7.34 million people when converting the rate into the number of patients.

Cancer is a disease currently ranking No. 1 for the cause of death in Korea and the number of new cancer patients for 1 year in 2009 according to data released by Statistics Korea on Dec. 30, 2011 was 192,561 (male: 99,224, female: 93,337), which had increased by 6.7% as compared to 180,465 in 2008 and by 90.6% as compared to 101,032 in 1999. For people in Korea, surviving to the age of 81, which is an average life span of people in Korea, the probability of suffering from cancers is 36.2%, and cancer has progressed in one of three patients (2 out of 5 male, and 1 out of 3 female). It was found that the total number of people with cancer surviving until the end of 2009 was 808,503, and the number of people overcoming cancer or living with cancer was 8 hundred thousand.

In accordance with Global Cancer Facts & Figures, 2nd Edition published by American Cancer Society in 2011, the cost for prevention, diagnosis, and treatment of cancer all over the world was estimated to be about 895 billion US dollars (985 trillion won in Korean money). It was investigated that cost incurred in relation with cancer in the US in 2010 was about 263.8 billion US dollars (290 trillion won in Korean money), the direct medical cost was 102.0 billion US dollars (112 trillion won in Korean money), the loss due to disease was 20.9 billion US dollars (23 trillion won in Korean money), and the economical loss due to premature death was 140.1 billion US dollars (154 trillion won in Korean money).

In accordance with cancer registry statistics released by the National Cancer Center in December, 2011, in Korea, it was estimated that the cost associated with cancer was: liver cancer (mean cost: 66.22 million won), lung cancer (46.47 million won), gastric cancer (26.85 million won) and colorectal cancer (23.52 million won).

A main reason that a normal cell is changed into a cancer cell is due to the abnormality of a gene, wherein the abnormality is caused by genetic factors inherited from parents; however, there are many cases where the abnormality is developed by acquired factors such as carcinogens, smoking, diet, virus infection, and the like. As a result, personal deviation in view of the reaction to chemotherapy after surgical procedure and the recurrence of cancer is largely shown. That is, since cancer is developed by reflecting genetic and environmental factors, cancer has patient-specific properties, and a degree of sensitivity to a specific drug also differs with each patient.

Hierarchial model, which is the latest theory with respect to cells configuring cancer tissue, asserts that a few tumor stem cells are present in tumor tissue and more differentiated cells without self reproduction ability are produced while maintaining a few tumor stem cells (E Passegue C. H. et al., Proc Natl Acad Sci USA, 30; 100 Suppl 1:11842-11849, 2003). Therefore, since a few tumor stem cells capable of inducing cancer and most of the differentiated cells losing cancer inducing ability are mixed, the tumor stem cell has drug resistance with respect to the conventional anti-cancer agents developed by having tumor cells occupying the majority in the cancer tissue as a target. As long as the tumor stem cell is present, the tumor may recur at any time, which is a key point of the tumor stem cell theory.

A theory of tumor stem cell was established by confirming the presence of the tumor stem cell in hematologic malignancy inducing leukemia for the first time in 1997 (Bonnet D. et al., Nat Med., 3(7):730-737, 1997). That is, it was confirmed that when cells determined as a cancer stem cell in an acute myeloid leukemia are extracted and transplanted into an immunosuppressive rat, human-derived leukemia is developed in a rat even with a small amount of cells. Then, evidence that tumor stem cells are present even in solid tumor cancers in breast cancer, colon cancer, prostate cancer, melanoma were suggested (Singh S. K. et al., Nature, 18; 432(7015):396-401, 2004).

The tumor stem cell has similar properties as a stem cell, for example, in the case of the acute myeloid leukemia, wherein cells having CD34+CD38-phenotype of hematopoietic stem cells have properties of the tumor stem cell (Bonnet D. et al., Nat Med., 3(7):730-737, 1997). In addition, brain tumor stem cells and normal nerve cells commonly express CD133, wherein CD133+ brain cancer cells even with 100 or less of a small amount thereof forms a tumor in the cranial cavity of a rat (Singh S. K. et al., Nature, 18; 432(7015):396-401, 2004; Kondo T. et al, Proc Natl Acad Sci USA, 20; 101(3):781-786, 2004). As another example of properties similar to stem cell, it is known that the brain tumor cell forms a sphere under specific conditions, like a nerve stem cell (Sanai N. et al., N Engl J Med., 353: 811-822, 2005). In addition, when serum is added to the brain tumor stem cell, the brain tumor stem cell may be similarly differentiated to the nerve stem cell (Rao J. S., Nat Rev Cancer, 3:489-501, 2003).

Meanwhile, in the case where expected effectiveness of an anti-cancer agent known to have excellent effects is not shown due to patient-specificity of cancer, trial and error for an appropriate treatment is inevitable, and risk and burdens of patients are increased. Thus, when a trial for reflecting personal characteristics in development and screening of an anti-cancer agent has been actively conducted, and it has been verified through various clinical tests that in the case where a customized targeted treatment having a target as a specific patient group is performed, treatment reaction of the patient is better than that of the existing standard anti-cancer treatment (Alterovitz G. et al., Oral Oncol., 47(10):951-5, 2011; Arnedos M. et al., Mol Oncol., 6(2):204-10, 2012; Black A. and Morris D., Curr Oncol., 19(Suppl 1):S73-85, 2012).

The beginning of the existing systematic drug screening method included injection of a mouse leukemia cell into an abdominal cavity and analysis of treatment effect of the drug at National Cancer Institute (NCI) in 1955 and establishment of a human cancer cell line xenograft transplantation model using immunodeficiency mouse established in the 1970s enables screening of main solid carcinoma (Hausser H. J. et al., Biochem Biophys Res Commun., 333:216-2, 2005). In 1989, NCI converted the basis of the screening strategy from a compound to a disease and then introduced an NCI-60 cell line panel consisting of human cancer cell lines having various histological and genetic properties, wherein in a retrospective analysis with respect to 39 drugs achieving up to clinical phase 2, in the case where over ⅓ of subcutaneous xenograft transplantation models show efficacy, it was reported that there is a significant relationship with a treatment reactivity in an actual patient (De Wever O. et al., J Pathol., 200:429-47, 2003).

However, since the above-described existing drug development system performs a drug screening based on a single cell line cultured in vitro for a long time, there are many cases where an efficacy of a developed drug is different from that in the actual clinical test. It is general that a proliferation assay constructing an anti-cancer agent screening is useful for evaluating an efficacy to an abnormal proliferation ability of a cancer cell; however, such has a limitation in reflecting sensitivity to the drug according to gene information. In particular, since a high throughput anti-cancer agent screening system constructed up to now demands an adherent culture of a cell onto an artifact surface, there is high probability of bringing genotypic and phenotypic changes and it is difficult to represent in an in vivo environment (US Patent Application Publication No. 2012-0077698). In order to overcome the above-described recent limitation, an effort to apply a three-dimensional culture to the high throughput screening system has been conducted; however, there are problems in that many cells are demanded for an analysis, and determination depends on a subjective determination of an inspector. In addition, in the case where the three-dimensional culture is a floating culture, since a focal distance for each area is different from each other, there are limitations in view of time and physical aspect in that each image should be taken from several thousands of wells for an automatic analysis (US Patent Application Publication No. 2009-0221441). Therefore, in order to precisely and rapidly conduct a screening method of anti-cancer materials with respect to various conditions, research into a technology of an automatic analysis method satisfying an environment capable of maximally maintaining properties of cancer cells, a demand on small number of cells, and an objective analysis is required.

Meanwhile, the genetically modified model and the xenograft transplantation model based on cancer cell lines among animal models easily cause a change in the cell lines, such that there are many cases of losing original properties as the cancer cell. In securing a required number of cell lines, the cell lines go through a long-time selection process under in vitro conditions. It was known that the above-described models are homogeneous and undifferentiated as compared to a tissue derived from an actual cancer patient (Hausser H. J. et al., Biochem Biophys Res Commun., 333:216-2, 2005). In addition, since human-derived stromal cells and immune cells configuring a microenvironment around cancer which is important for growth and metastasis of cancer are absent, original biological and molecular properties of a patient carcinoma are not reproduced any more (De Wever O. et al., J Pathol., 200:429-47, 2003).

As a useful method for overcoming the problem, patient-derived tumografts in which surgically removed patient-derived tumor tissue is directly transplanted into an immunodeficiency mouse was suggested (Rubio-Viqueira B. and Hidalgo M., Clin Pharmacol Ther., 85:217-21, 2009; Fichtner I et al., Eur J Cancer., 40:298-307, 2004). Since both of the cancer tissue and the stromal cell of microenvironment around cancer are derived from the same patient, the patient-derived tumorgrafts are evaluated as being that transplantation success, growth of cancer tissue, and reaction to drug are most similarly reproduced. However, about 90% of anti-cancer agents showing a remarkable anti-cancer effect in a preclinical model and entering a clinical test are not capable of reproducing effects in actual patients up to the present.

Therefore, in order to develop a screening method for effectively selecting an optimal anti-cancer agent and an optimal combination of anti-cancer agents with respect to an individual patient, a technology capable of reflecting gene information of a patient, mimicking an environment in a human body, and efficiently analyzing a large amount of samples is needed.

Accordingly, the present inventors made an effort to solve the problems of the related art as described above. As a result, the present inventors confirmed that in the case where a patient-derived cancer cell is subjected to a screening method including three-dimensional culture using a limiting dilution assay, patient-specific anti-cancer agents are capable of being efficiently selected by using an extremely small amount of cells as compared to the existing screening methods, thereby completing the present invention.

SUMMARY

An object of the present invention is to provide an efficient screening method of patient-specific anti-cancer agents.

Another object of the present invention is to provide a method of confirming an anti-cancer effect of a patient-specific anti-cancer agent candidate group in an animal model containing patient-derived cancer cells.

In order to achieve the foregoing objects, the present invention provides a method for screening patient-specific anti-cancer agents comprising: (a) three-dimensionally culturing cancer cells isolated from patient-derived cancer tissues into 0.01 to 0.1 μl of hydrogel; (b) treating the three-dimensionally cultured cancer cells with candidate anti-cancer agents; and (c) confirming whether or not spheres of the cancer cells are formed, and selecting the candidate anti-cancer agent as a patient-specific anti-cancer agent, which is confirmed to show a sphere-forming inhibitory activity.

In addition, the present invention provides a method for screening patient-specific anti-cancer agents comprising: (a) three-dimensionally culturing cancer cells isolated from patient-derived cancer tissue into 0.01 to 0.1 µl of hydrogel; (b) treating the three-dimensionally cultured cancer cell with a candidate anti-cancer agent; (c) confirming whether or not spheres of the cancer cells are formed, and selecting the candidate anti-cancer agent as a patient-specific anti-cancer agent, which is confirmed to show a sphere-forming inhibitory activity; and (d) treating an animal model containing patient-derived cancer stem cells with the patient-specific anti-cancer agent selected in the step (c) and confirming an anti-cancer effect.

According to the present invention, since the patient-specific anti-cancer agents reflecting individual genetic properties may be precisely and rapidly selected by using an extremely small amount of cancer cells, the screening method of the patient-specific anti-cancer agents according to the present invention is useful for development of novel anti-cancer agents and in the personalized medical field.

DETAILED DESCRIPTION

Figure 1:
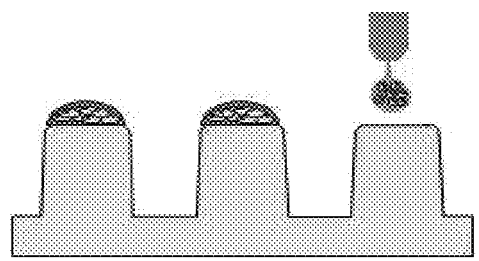
FIG. 1 is a schematic view showing a process of fixing hydrogel containing cells onto a micropillar.

In the present invention, in order to screen patient-derived specific anti-cancer agents, cancer cells isolated from patient-derived cancer tissues were subjected to three-dimensional culture using a limiting dilution assay (LDA), the three-dimensionally cultured cancer cells were treated with a candidate anti-cancer agent, and a sphere-forming inhibitory activity of the treated candidate anti-cancer agent was confirmed.

In an embodiment of the present invention, cancer cells isolated from tumor tissues of a brain glioblastoma patient were mixed into hydrogel and then subjected to three-dimensional culture onto a micropillar, and then, the three-dimensionally cultured cancer cells were exposed to a candidate drug under various conditions and the degree of forming spheres of cancer cells was determined.

In the present invention, the term "sphere" indicates cell agglomerate formed from some cells having properties similar to stem cells among cells configuring cancer tissues, under a three-dimensional culture condition.

Therefore, an aspect of the present invention provides a screening method of patient-specific anti-cancer agents comprising (a) three-dimensionally culturing cancer cells isolated from patient-derived cancer tissues into 0.01 to 0.1 µl of hydrogel; (b) treating the three-dimensionally cultured cancer cells with candidate anti-cancer agents; and (c) confirming whether or not spheres of the cancer cells are formed, and selecting the candidate anti-cancer agent as a patient-specific anti-cancer agent, which is confirmed to show a sphere-forming inhibitory activity.

It is characterized that a cancer of the present invention is a solid tumor cancer.

The solid tumor cancer is preferably selected from a group consisting of a liver cancer, a gliocytoma, an ovarian cancer, a colon cancer, a head and neck cancer, a bladder cancer, a renal cell cancer, a gastric cancer, a breast cancer, a metastatic cancer, a prostate cancer, a pancreatic cancer and a lung cancer.

It is characterized that the cancer cells isolated form the patient-derived cancer tissues of the present invention are obtained by (a) pulverizing the isolated cancer patient-derived cancer tissues, followed by obtaining cell fractions from the pulverized materials; and (b) treating the obtained cell fractions with protease, followed by filtration, centrifugation, and suspension to obtain a single cell.

It is characterized that the cancer cell of the present invention contains a cancer stem cell.

It is characterized that the cancer stem cell forms a sphere from a single cell after the three-dimensional culturing.

It is characterized that a hydrogel of the present invention is an alginate.

It is characterized that the hydrogel of the present invention contains 1 to 300 cancer cells with each concentration gradient.

It is characterized that whether or not the sphere is formed in the present invention is confirmed by measuring sphere areas.

It is characterized that the sphere has a size of 10 µm to 100 µm.

It is characterized that in the confirmation of whether or not the sphere is formed, in a case where the sphere area is smaller than an average area of control group spheres, it is determined that the spheres are not formed.

It is characterized that the average area of the control group spheres is an average value of the biggest spheres among the control group spheres formed in each hydrogel.

It is characterized that the control group spheres are formed from 5 to 50 patient-derived cancer cells which are not treated with the anti-cancer agent.

Another aspect of the present invention provides a screening method of patient-specific anti-cancer agents including (a) three-dimensionally culturing cancer cells isolated from patient-derived cancer tissue into 0.01 to 0.1 µl of hydrogel; (b) treating the three-dimensionally cultured cancer cell with a candidate anti-cancer agent; (c) confirming whether or not spheres of the cancer cells are formed, and selecting the candidate anti-cancer agent as a patient-specific anti-cancer agent, which is confirmed to show a sphere-forming inhibitory activity; and (d) treating an animal model containing patient-derived cancer stem cells with the patient-specific anti-cancer agent selected in the step (c) and confirming an anti-cancer effect.

It is characterized that an animal of the present invention is an immunodeficiency mouse.

The immunodeficiency mouse is preferably a nude mouse, a non-obese diabetic (NOD) mouse, a severe combined immunodeficiency (SCID) mouse, an NOD-SCID mouse or an NOG (NOD/SCID Il2rg-/-) mouse.

It is characterized that a cancer of the present invention is a solid tumor cancer.

The solid tumor cancer is preferably selected from a group consisting of a liver cancer, a gliocytoma, an ovarian cancer, a colon cancer, a head and neck cancer, a bladder cancer, a renal cell cancer, a gastric cancer, a breast cancer, a metastatic cancer, a prostate cancer, a pancreatic cancer and a lung cancer.

The cancer cells isolated from the patient-derived cancer tissues of the present invention are obtained by ((a) pulverizing the isolated cancer patient-derived cancer tissues, followed by obtaining cell fractions from the pulverized materials; and (b) treating the obtained cell fractions with protease, followed by filtration, centrifugation, and suspension to obtain a single cell.

It is characterized that the cancer cell of the present invention contains a cancer stem cell.

It is characterized that the cancer stem cell forms a sphere from a single cell after the three-dimensional culturing.

It is characterized that a hydrogel of the present invention is an alginate.

It is characterized that the hydrogel of the present invention contains 1 to 300 cancer cells with each concentration gradient.

It is characterized that whether or not the sphere is formed in the present invention is confirmed by measuring sphere areas.

It is characterized that the sphere has a size of 10 μm to 100 μm.

It is characterized that in the confirmation of whether or not the sphere is formed, in a case where the sphere area is smaller than an average area of control group spheres, it is determined that the spheres are not formed.

It is characterized that the average area of the control group spheres is an average value of the biggest spheres among the control group spheres formed in each hydrogel.

It is characterized that the control group spheres are formed from 5 to 50 patient-derived cancer cells which are not treated with the anti-cancer agent.

Hereinafter, the present invention will be described in detail with reference to the following Examples. These examples are only for exemplifying the present invention, and it will be obvious to those skilled in the art that the scope of the present invention is not construed to be limited to these examples.

EXAMPLES

Example 1

Isolation and Culture of Cells

Tumor tissues extracted from a surgical process of a brain glioblastoma patient were washed with PBS within 6 hours, and mechanically pulverized using surgical scissors or an automatic pulverization device. The pulverized tumor tissues were subjected to enzymatic degradation by being treated with collagenase (Invitrogen, US) and trypsin (Invitrogen, US). The dissociated tissues were subjected to centrifugation under a condition of 400×g for 3 minutes, the obtained precipitate was washed with PBS several times and passed through pore size nylon mesh having a pore size of 100 μm, thereby obtaining a cell suspension dissociated at a level of a single cell.

For culture of cancer cells, the obtained reactant was subjected to suspension-culture at a concentration of 1~3×$10^5$ cells/ml using a nerve stem cell culture medium (Neurobasal-A) [Gibco, US] containing cell growth factor (bFGF/EGF) [R&D systems, US] and additive (L-glutamine/B27/N2) (Gibco, US), thereby securing neurospheres. Cancer cell lines isolated from tissues of three patients according to the above-described method are designated as 448T, 464T and 775T, respectively.

Example 2

Coating of Micropillar Chip

A surface of ends of a micropillar chip (Samsung Electro-Mechanics Co., Korea) was modified so that hydrogel containing cells at the time of performing a three-dimensional culture of a patient-derived cancer cell was not desorbed. Each 60 nl of 0.01% poly-L-lysine (Sigma-Aldrich, US) was discharged onto the ends of the micropillar using a microarray spotter (Samsung Electro-Mechanics Co., Korea), followed by incubation in a humid chamber for 1 hour. After incubation, PLL-coated pillarchip was washed with Dulbecco's phosphate buffered saline buffer (Invitrogen, US), and dried at room temperature. Then, 60 nl of 0.05% $BaCl_2$ solution (Sigma-Aldrich, US) was discharged onto the PLL-coated pillarchip so that alginate droplet was not desorbed.

Example 3

Three-Dimensional Culture of Patient-Derived Cancer Cell

The suspension-cultured neurospheres obtained in Example above were collected and treated with 0.025% trypsin/EDTA for 3 minutes, thereby obtaining cell suspensions at a level of a single cell. The cell suspensions were prepared at a concentration of 4 cells/30 nl, 10 cells/30 nl, 20 cells/30 nl, 40 cells/30 nl, 100 cells/30 nl and 200 cells/30 nl, respectively.

50 μL of 3% alginate (Sigma-Aldrich, US) and 100 μL distilled water were mixed to prepare 1% alginate, and then the cell suspensions and 1% alginate as prepared above were mixed together in the same amount. The prepared alginate/cell mixture was discharged onto the surface-modified micropillar using a microarray spotter (Samsung Electro-Mechanics Co., Korea), followed by gelation for 2 minutes so that an alginate gel containing 2, 5, 10, 20, 50 or 100 cells was fixed onto each micropillar (FIG. 1).

Example 4

Treatment with Anti-Cancer Agent

Each of 950 nl of 2 μM, 5 μM or 10 μM SU11274 (Sigma-Aldrich, US) was dispersed into a microwell chip (Samsung Electro-Mechanics Co., Korea) and the micropillar chip was subjected to stamping. The prepared micropillar chip/microwell chip was put into a gas-permeable incubation chamber (Samsung Electro-Mechanics Co., Korea) and cultured in $CO_2$ incubator for 12 days.

Example 5

Sphere Staining 4 doubling time incubation was performed until spheres were formed from the patient-derived cancer cells, and the micropillar chip was subjected to fluorescence staining. The micropillar chip was washed with a staining buffer (140 mM NaCl with 20 mM $CaCl_2$) twice for each 5 minutes, and then stained by Calcein AM (Invitrogen, US) at room temperature for 45 minutes. In order to remove excess dye present in alginate spot, the micropillar chip was washed with the staining buffer twice for 15 minutes, and dried at room temperature for 2 hours or more. The dried micropillar chip was subjected to an image scan (S+ Chip Scanner: Samsung Electro-Mechanics Co., Korea) under a condition of 475 nm±35 nm excitation filter and 530 nm±43 nm emission filter.

Figure 2:
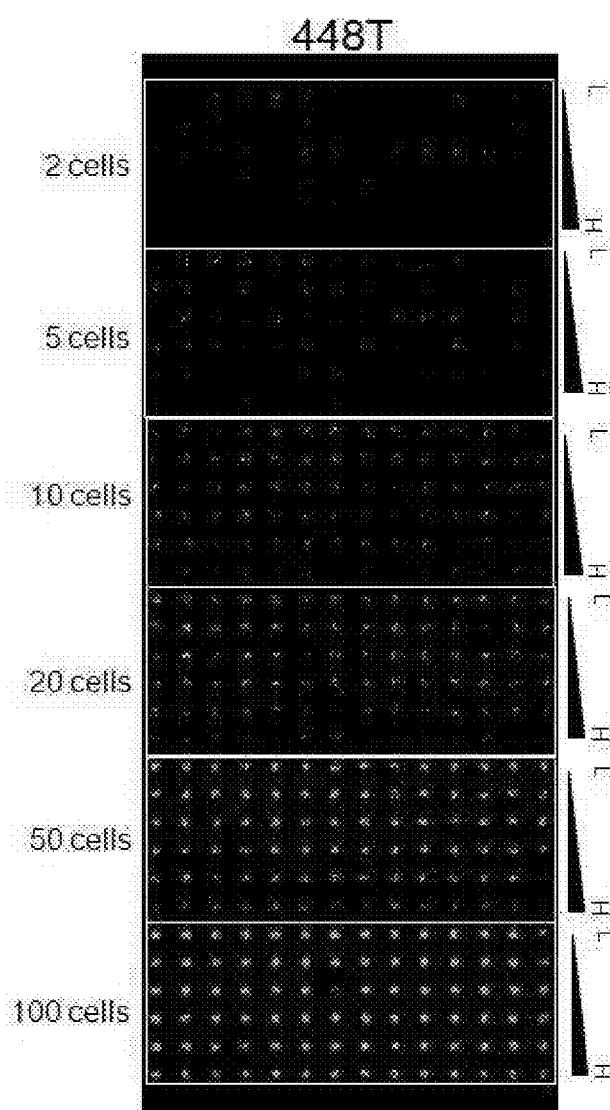
FIG. 2 is a photograph of fluorescence stained spheres showing spheres formed after performing a screening method using a limiting dilution assay.

As a result, performing one test using an excessively small amount of $1.5 \times 10^4$ cancer cells under 504 experimental conditions was possible, and it was observed that as concentration of SU11274 became increased under the condition with each number of cells, the survival rate of the cancer cells were decreased (FIG. 2).

Figure 3:
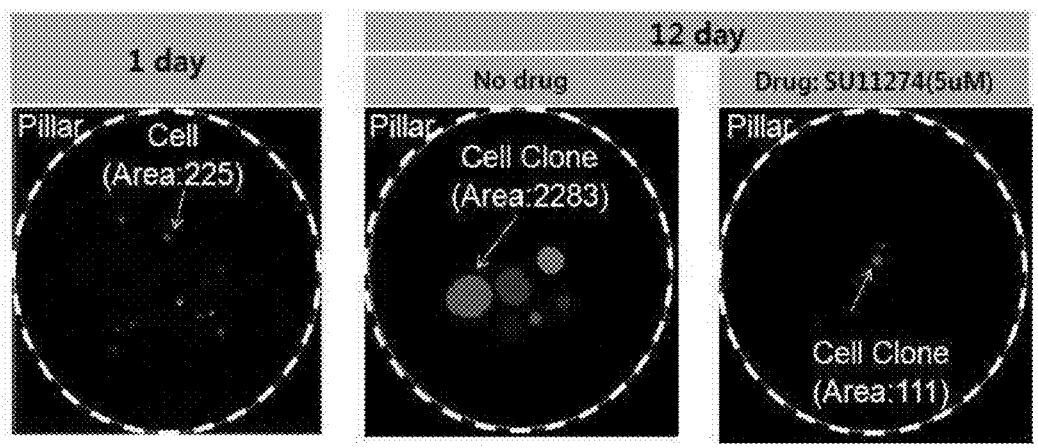
FIG. 3 shows results obtained by measuring sphere areas by automatically analyzing the fluorescent photograph of the spheres using a program for an auto-analysis.

Using a program of S+ Chip Analysis (Samsung Electro-Mechanics Co., Korea), spheres stained by Calcein AM were divided into different colors according to each size thereof and the maximum sphere size present in each micropillar was deduced. As a result, it was observed that the patient-derived cancer cells of a control group formed spheres and the sphere areas were increased to the maximum of 10.14 times for 12 days; however, cancer cells of an experiment group treated with 5 uM SU11274 did not form the spheres (FIG. 3).

Example 6

Screening of Anti-Cancer Agent

The patient-specific anti-cancer agent was screened by using a limiting dilution assay according to the above-described Examples, and a result obtained therefrom was compared with a result separately obtained by a screening method using a 96 well plate. Alginate gel containing 2, 5, 10, 20, 50 or 100 cells was discharged onto each micropillar and was subjected to stamping into a culture medium containing the anti-cancer agent. The anti-cancer agent SU11274 and PHA665752, which is c-Met inhibitor, was treated for each concentration. A size of spheres formed after being cultured for 2 to 3 weeks was automatically measured and analyzed.

Figure 4:
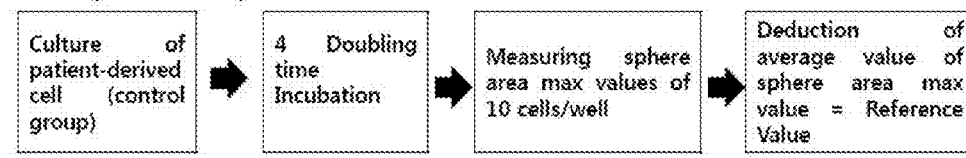
FIG. 4 shows an outline of LDA analysis program showing a method for determining whether or not the spheres are formed after culturing cancer cells.
Figure 4:
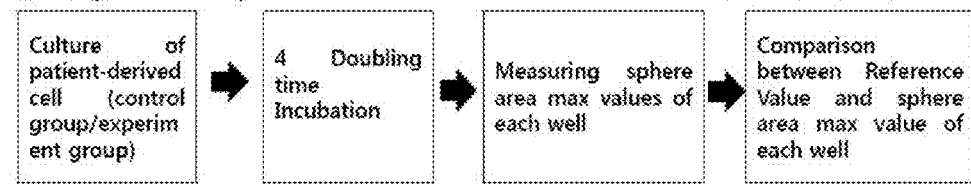
Figure 4:
Figure 5:
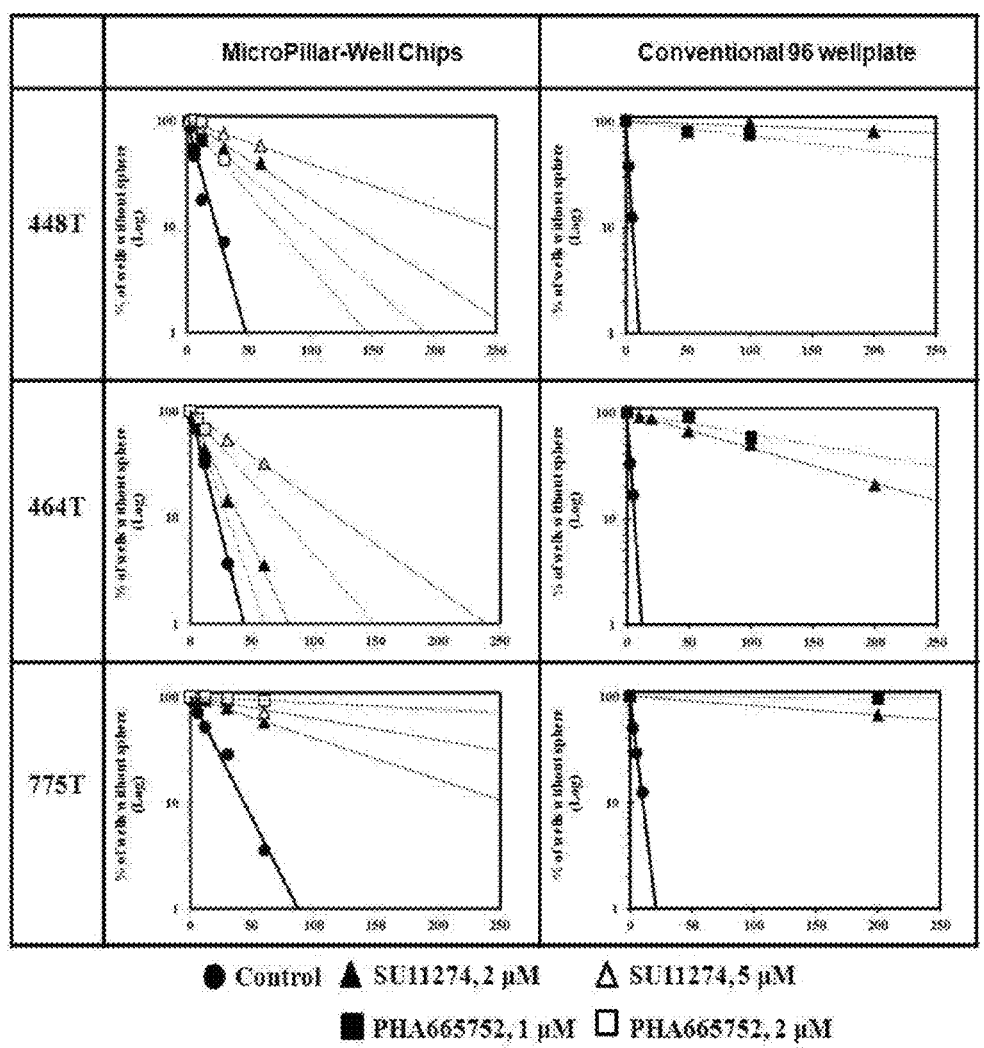
FIG. 5 shows results obtained by comparison of a screening method of an anti-cancer agent with respect to patient-derived cancer cells between the present invention and the related art.

Whether or not the sphere is formed was determined by culturing cells of the experimental group and the control group up to 4 doubling times and comparing sphere area max values of the biggest spheres among the spheres formed in each well, as shown in FIG. 4. A 'reference value' means an average value of sphere area max values deduced from each well after the control group cells were cultured at a concentration of 10 cells/well. Here, the well having sphere area max value smaller than the reference value was determined that the spheres were not formed in the well (non-formed). The well having sphere area max value as the same as the average value of the sphere area max of the control group or higher than that was determined that the sphere were formed in the well (formed). After determination, a ratio of the well determined as non-formed was set as an Y axis, and the number of initially inoculated cells was set as an X axis, and then the result was analyzed (FIG. 5). That is, since the ratio of the micropillar in which the spheres were not formed was set as an Y axis, and the number of cells required for forming the spheres was set as an X axis, as an effect of the candidate anti-cancer agent showing excellent anti-cancer effect, the number of cells required for forming the spheres was increased, and thus, slope of a trend line was decreased as compared to the control group.

It was confirmed from the result obtained by the screening method that 775T cell line showed the most sensitive anti-cancer effects to SU11274 and PHA665752 as compared to 448T and 464T cell lines, such that even though the cancer cells were isolated from the same brain glioblastoma, the effects of the anti-cancer agents were different depending on patients. In the screening method using the conventional 96 well, the effects between the anti-cancer agents were similar to about 10% in every result of cell lines, such that determination ability was not significantly shown (FIG. 5).

Therefore, it was proved that the screening method using the limitation dilution assay of the present invention may rapidly and precisely screen the patient-specific anti-cancer agent composition optimized according to individual patient. In addition, a probability of success in clinical trials may be largely increased by applying the anti-cancer agents screened by the above-described method to an animal model into which the patient-derived cancer is transplanted.

The present invention has been described in detail based on particular features thereof, and it is obvious to those skilled in the art that these specific technologies are merely preferable embodiments and thus the scope of the present invention is not limited to the embodiments. Therefore, the substantial scope of the present invention is defined by the accompanying claims and equivalent thereof.

What is claimed is:

1. A method of identifying a potential patient-specific anti-gliocytoma agent using a micropillar chip, the method comprising:
    (a) isolating gliocytoma cells from gliocytoma tissue of a patient having the gliocytoma tissue, wherein the gliocytoma cells include cancer stem cells;
    (b) creating three-dimensional hydrogel matrices wherein each of the matrices comprises a gradient of increasing concentrations of the isolated gliocytoma cells wherein the hydrogel is in a volume of the matrix from 0.01 to 0.1 μl and the gradients are arranged in increasing concentrations of from 2 of the isolated gliocytoma cells to 300 of the gliocytoma cells wherein each of the three-dimensional hydrogel matrices are coated onto a pillar of a micropillar chip;
    (c) treating each of the pillars comprising the hydrogel matrices with candidate anti-gliocytoma agents and culturing the agent comprising micropillar chips; and
    (d) assaying the treated gliocytoma cells by measuring sphere areas using an image scanner, and selecting an agent from the candidate agents when the measured sphere area demonstrates a reduced spherical cell formation compared to control cells as the potential patient-specific anti-gliocytoma agent, wherein the control cells are gliocytoma cells isolated from the gliocytoma tissue of the patient cultured on the hydrogel matrices in the absence of treatment by potential anti-gliocytoma agents.

2. The method according to claim 1, wherein the gliocytoma cells isolated from the gliocytoma tissue of the patient are obtained as single cells by (a) pulverizing the gliocytoma tissue to obtain a pulverized tissue material, (b) obtaining cell fractions from the pulverized material; and (c) treating the obtained cell fractions with protease, followed by filtration, centrifugation, and suspension to obtain the single cells.

3. The method according to claim 1, wherein the hydrogel is an alginate.

4. The method according to claim 1, wherein each of the concentration gradients comprises a cell density of 2, 5, 10, 20, 50, 100, 150, 200 or 300 gliocytoma cells.

5. The method according to claim 1, wherein the measured sphere areas of the treated gliocytoma cells have a size in a range of from 10 μm to 100 μm.

6. The method according to claim 1, wherein step (d) comprises culturing the micropillars of the treated gliocytoma cells and the micropillars of the cultured cells up to 4 doubling times prior to assaying wherein the comparison of step (d) is between the biggest sphere of the treated gliocytoma cells and the biggest sphere of the control cells.

7. A method of identifying a potential patient-specific anti-gliocytoma agent using a micropillar chip, the method comprising:
   (a) isolating gliocytoma cells from gliocytoma tissue of a patient having the gliocytoma tissue, wherein the gliocytoma cells include cancer stem cells;
   (b) creating three-dimensional hydrogel matrices wherein each of the matrices comprises a gradient of increasing concentrations of the isolated gliocytoma cells wherein the hydrogel is in a volume of the matrix from 0.01 to 0.1 μl and the gradients are arranged in increasing concentrations from 2 of the isolated gliocytoma cells to 300 of the gliocytoma cells wherein each of the three-dimensional hydrogel matrices are coated onto a pillar of a micropillar chip;
   (c) treating each of the pillars comprising the hydrogel matrices with candidate anti-gliocytoma agents and culturing the agent comprising micropillar chips;
   (d) assaying the treated gliocytoma cells by measuring sphere areas using an image scanner, and selecting an agent from the candidate agents when the measured sphere area demonstrates a reduced spherical cell formation compared to control cells as the potential patient-specific anti-gliocytoma agent wherein the control cells are gliocytoma cells isolated from the gliocytoma tissue of the patient cultured on the hydrogel matrices in the absence of treatment by potential anti-gliocytoma agents; and
   (e) treating an animal model containing the isolated gliocytoma cells of the patient with the patient-specific anti-gliocytoma agent selected in step (d) and confirming reduced spherical cell formation in the animal model treated with the potential patient-specific anti-gliocytoma agent compared to a control animal model, wherein the control animal model contains gliocytoma cells isolated from the gliocytoma tissue of the patient cultured on the hydrogel matrices in the absence of treatment by potential anti-gliocytoma agents.

8. The method according to claim 7, wherein the animal is an immunodeficiency mouse.

9. The method according to claim 8, wherein the immunodeficiency mouse is a nude mouse, a non-obese diabetic (NOD) mouse, a severe combined immunodeficiency (SCID) mouse, an NOD-SCID mouse or an NOG (NOD/SCID I12rg−/−) mouse.

10. The method according to claim 7, wherein the gliocytoma cells isolated from the patient-derived gliocytoma tissues are obtained as single cells by (a) pulverizing the gliocytoma tissue to obtain a pulverized tissue material, (b) obtaining cell fractions from the pulverized material; and (c) treating the obtained cell fractions with protease, followed by filtration, centrifugation, and suspension to obtain the single cells.

11. The method according to claim 7, wherein the hydrogel is an alginate.

12. The method according to claim 7, wherein each of the concentration gradients comprises a cell density of 2, 5, 10, 20, 50, 100, 150, 200 or 300 gliocytoma cells.

13. The method according to claim 7, wherein the measured sphere areas of the treated gliocytoma cells have a size in a range of from 10 μm to 100 μm.

14. The method according to claim 7, wherein step (d) comprises culturing the micropillars of the treated gliocytoma cells and the micropillars of the cultured cells up to 4 doubling times prior to assaying wherein the comparison of step (d) is between the biggest sphere of the treated gliocytoma cells and the biggest sphere of the control cells.

\* \* \* \* \*

UNITED STATES PATENT AND TRADEMARK OFFICE
CERTIFICATE OF CORRECTION

PATENT NO. : 9,562,891 B2
APPLICATION NO. : 14/228205
DATED : February 7, 2017
INVENTOR(S) : Nam et al.

Page 1 of 1

It is certified that error appears in the above-identified patent and that said Letters Patent is hereby corrected as shown below:

In the Specification

Column 8, Line 34: delete "Example above" and insert --Example 1 above--.

Signed and Sealed this
Twenty-eighth Day of March, 2017

Michelle K. Lee
*Director of the United States Patent and Trademark Office*